(12) United States Patent
Shi et al.

(10) Patent No.: US 7,103,484 B1
(45) Date of Patent: Sep. 5, 2006

(54) NON-CONTACT METHODS FOR MEASURING ELECTRICAL THICKNESS AND DETERMINING NITROGEN CONTENT OF INSULATING FILMS

(75) Inventors: Jianou Shi, Milpitas, CA (US); Steve Yifeng Cui, Fremont, CA (US); Shiyou Pei, Saratoga, CA (US); Zhiwei (Steve) Xu, Sunnyvale, CA (US); Haiyong (Howard) Wang, Pleasanton, CA (US)

(73) Assignee: KLA-Tencor Technologies Corp., Milpitas, CA (US)

( * ) Notice: Subject to any disclaimer, the term of this patent is extended or adjusted under 35 U.S.C. 154(b) by 44 days.

(21) Appl. No.: 10/698,222

(22) Filed: Oct. 31, 2003

(51) Int. Cl.
 *G01R 15/00* (2006.01)
 *G01R 31/26* (2006.01)

(52) U.S. Cl. .......................... 702/57; 438/17
(58) Field of Classification Search ................ 702/57; 324/671, 455, 765; 438/17, 16
See application file for complete search history.

(56) References Cited

U.S. PATENT DOCUMENTS

| | | | |
|---|---|---|---|
| 3,495,269 A | 2/1970 | Mutschler et al. .......... 347/126 |
| 3,496,352 A | 2/1970 | Jugle .......................... 399/100 |
| 4,015,203 A | 3/1977 | Verkuil ....................... 324/254 |
| 4,599,558 A | 7/1986 | Castellano et al. ......... 324/752 |
| 4,734,721 A | 3/1988 | Boyer et al. ................ 347/126 |
| 4,812,756 A | 3/1989 | Curtis et al. ................ 324/750 |
| 5,485,091 A | 1/1996 | Verkuil ....................... 324/455 |
| 5,498,974 A * | 3/1996 | Verkuil et al. .............. 324/767 |
| 5,528,153 A * | 6/1996 | Taylor et al. ............... 324/671 |
| 5,594,247 A | 1/1997 | Verkuil et al. .............. 250/326 |
| 5,644,223 A | 7/1997 | Verkuil ....................... 324/158.1 |
| 5,650,731 A | 7/1997 | Fung ............................ 324/752 |
| 5,661,408 A | 8/1997 | Kamieniecki et al. ...... 324/765 |
| 5,742,658 A | 4/1998 | Tiffin et al. .................... 378/44 |
| 5,767,691 A | 6/1998 | Verkuil ........................ 324/761 |
| 5,767,693 A | 6/1998 | Verkuil ........................ 324/767 |
| 5,773,989 A | 6/1998 | Edelman et al. ............ 324/765 |

(Continued)

FOREIGN PATENT DOCUMENTS

WO 98/57358 12/1998

OTHER PUBLICATIONS

Schroder, Contactless Surface Charge Semiconductor Characterization, Apr. 2002, Materials Science and Engineering B, vol. 91-92, pp. 196-228.*

(Continued)

*Primary Examiner*—Bryan Bui
*Assistant Examiner*—Toan M. Le
(74) *Attorney, Agent, or Firm*—Ann Marie Mewherter; Daffer McDaniel, LLP (57) ABSTRACT

Non-contact methods for determining a parameter of an insulating film are provided. One method includes measuring at least two surface voltages of the insulating film. The surface voltages are measured after different charge depositions. Measuring the surface voltages is performed in two or more sequences. The method also includes determining individual parameters for the two or more sequences from the surface voltages and the charge depositions. In addition, the method includes determining the parameter of the insulating film as an average of the individual parameters. The parameter is substantially independent of leakage in the insulating film. Another method includes determining a characteristic of nitrogen in an insulating film using two parameters of the insulating film selected from equivalent oxide thickness, optical thickness, and a measure of leakage through the insulating film. The characteristic may be a nitrogen dose, a nitrogen percentage, or a presence of nitrogen in the insulating film.

25 Claims, 6 Drawing Sheets

U.S. PATENT DOCUMENTS

| | | | | |
|---|---|---|---|---|
| 5,834,941 | A | 11/1998 | Verkuil | 324/455 |
| 5,852,232 | A | 12/1998 | Samsavar et al. | 73/105 |
| 5,866,806 | A | 2/1999 | Samsavar et al. | 73/105 |
| 5,948,972 | A | 9/1999 | Samsavar et al. | 73/105 |
| 5,955,661 | A | 9/1999 | Samsavar et al. | 73/105 |
| 6,011,404 | A | 1/2000 | Ma et al. | 324/765 |
| 6,060,709 | A | 5/2000 | Verkuil et al. | 250/326 |
| 6,072,320 | A | 6/2000 | Verkuil | 324/750 |
| 6,091,257 | A | 7/2000 | Verkuil et al. | 324/765 |
| 6,097,196 | A | 8/2000 | Verkuil et al. | 324/750 |
| 6,104,206 | A | 8/2000 | Verkuil | 324/765 |
| 6,121,783 | A | 9/2000 | Horner et al. | 324/757 |
| 6,191,605 | B1 | 2/2001 | Miller et al. | 324/767 |
| 6,201,999 | B1 | 3/2001 | Jevtic | 700/100 |
| 6,202,029 | B1 | 3/2001 | Verkuil et al. | 702/64 |
| 6,224,638 | B1 | 5/2001 | Jevtic et al. | 29/25.01 |
| 6,267,005 | B1 | 7/2001 | Samsavar et al. | 73/105 |
| 6,569,691 | B1 | 5/2003 | Jastrzebski et al. | 438/14 |
| 6,593,748 | B1 * | 7/2003 | Halliyal et al. | 324/455 |
| 6,597,193 | B1 * | 7/2003 | Lagowski et al. | 324/765 |
| 6,642,066 | B1 * | 11/2003 | Halliyal et al. | 438/16 |
| 6,680,621 | B1 * | 1/2004 | Savtchouk et al. | 324/765 |
| 6,734,696 | B1 * | 5/2004 | Horner et al. | 324/765 |
| 6,915,232 | B1 * | 7/2005 | Kitajima et al. | 702/171 |
| 2002/0090746 | A1 | 7/2002 | Xu et al. | |

OTHER PUBLICATIONS

Schroder et al., Corona-Oxide-Semiconductor Device Characterization, 1998, Solid-State Electronics, vol. 42, No. 4, pp. 505-512.*

Hung et al., Metrology Study of Sub 20 Angstrom Oxynitride by Corona-Oxide-Silicon (COS) and Conventional C-V Approaches, 2002, Mat. Res. Soc. Symp. Proc., vol. 716, pp. 119-124.*

Cosway et al., "Manufacturing Implementation of Corona Oxide Silicon (COS) Systems for Diffusion Furnace Contamination Monitoring," 1997 IEEE/SEMI Advanced Semiconductor Manufacturing Conference, pp. 98-102.

Miller, "A New Approach for Measuring Oxide Thickness," Semiconductor International, Jul. 1995, pp. 147-148.

*Numerical Recipies in C, The Art of Scientific Computing, 2nd Ed.,* © Cambridge University Press 1988, 1992, p. 683.

Weinberg, "Tunneling of Electrons from Si into Thermallly Grown $SiO_2$," Solid-State Electronics, 1977, vol. 20, pp. 11-18.

Verkuil, "Rapid Contactless Method for Measuring Fixed Oxide Charge Associated with Silicon Processing," IBM Technical Disclosure Bulletin, vol. 24, No. 6, 1981, pp. 3048-3053.

"Contactless Photovoltage vs. Bias Method for Determining Flat-Band Voltage," IBM Technical Disclosure Bulletin, vol. 32, vol. 9A, 1990, pp. 14-17.

"Contactless Electrical Equivalent Oxide Thickness Measurement," IBM Technical Disclosure Bulletin, vol. 29, No. 10, 1987, pp. 4622-4623.

Diebold et al., "Characterization and production metrology of thin transistor gate oxide films," Materials Science in Semiconductor Processing 2, 1999, pp. 103-147.

Comizzoli, "Uses of Corona Discharge in the Semiconductor Industry," J. Electrochem. Soc., 1987, pp. 424-429.

Verkuil et al., "A Contactless Alternative to MOS Charge Measurements by Means of a Corona-Oxide-Semiconductor (COS) Technique," Electrochem. Soc. Extended Abstracts, 1988, vol. 88-1, No. 169, pp. 261-262.

Weinzierl et al., "Non-Contact Corona-Based Process Control Measurements; Where We've Been, Where We're Headed," Electrochemical Society Proceedings, Oct. 1999, vol. 99-16, pp. 342-350.

Schroder, "Surface voltage and surface photovoltage: history, theory and applications," Measurement Science and Technology, vol. 12, 2001, pp. R16-31.

* cited by examiner

NON-CONTACT METHODS FOR MEASURING ELECTRICAL THICKNESS AND DETERMINING NITROGEN CONTENT OF INSULATING FILMS

BACKGROUND OF THE INVENTION

1. Field of the Invention

This invention generally relates to determining an electrical parameter and/or nitrogen content of an insulating film. Certain embodiments relate to determining one or more electrical parameters and the nitrogen content of an insulating film that is imperfectly insulating.

2. Description of the Related Art

Fabricating semiconductor devices such as logic and memory devices typically includes processing a substrate such as a semiconductor wafer using a number of semiconductor fabrication processes to form various features and multiple levels of the semiconductor devices. For example, insulating (or dielectric) films may be formed on multiple levels of a substrate using deposition processes such as chemical vapor deposition (CVD), physical vapor deposition (PVD), and atomic layer deposition (ALD). In addition, insulating films may be formed on multiple levels of a substrate using a thermal growth process. For example, a layer of silicon dioxide may be thermally grown on a substrate by heating the substrate to a temperature of greater than about 700° C. in an oxidizing ambient such as $O_2$ or $H_2O$. Such insulating films may electrically isolate conductive structures of a semiconductor device formed on the substrate.

Measuring and controlling such insulating films is an important aspect of semiconductor device manufacturing. A number of techniques are presently available for making such measurements. For example, electrical measurement techniques that rely on physical contact to a conductive electrode on top of an insulating film may be used to determine relevant electrical properties of insulating films using capacitance vs. voltage (C-V) and current vs. voltage (I-V) measurements. Such measurements have a long history and established utility. These measurements, however, require a conductive electrode and a contacting probe. The necessity of direct physical electrical contact is particularly undesirable in many manufacturing situations.

Non-contacting electrical test techniques have been developed to provide electrical capacitance, electrical thickness, and electrical conductivity information about insulating films. Non-contacting electrical measurements of dielectric properties have the unique advantage of providing electrically derived information without the requirement of physical contact to an electrode on top of an insulating film. These techniques typically use an ion generation source such as a corona and a non-contacting voltage measurement sensor such as a Kelvin Probe or a Monroe Probe to determine electrical properties of the films. Examples of such techniques are illustrated in U.S. Pat. No. 5,485,091 to Verkuil, U.S. Pat. No. 6,097,196 to Verkuil et al., and U.S. Pat. No. 6,202,029 to Verkuil et al., which are incorporated by reference as if fully set forth herein. Additional examples of such measurements can be found in "Non-Contact Corona-Based Process Control Measurements: Where We've Been, Where We're Headed," by Steven R. Weinzierl and Tom G. Miller, *Proceedings of the 196th Meeting of The Electrochemical Society*, invited presentation, 17–22 Oct., 1999, Honolulu, Hi. and "Uses of Corona Discharges in the Semiconductor Industry," by R. G. Comizzoli, *J. Electrochem. Soc.*, February, 1987, pp. 424–429, which are incorporated by reference as if fully set forth herein.

One example of a non-contact metrology tool is the Quantox™ system, which is commercially available from KLA-Tencor, San Jose, Calif. This metrology tool is configured to measure gate electrical properties based on the non-contact Kelvin probe measurement principles. Examples of non-contact Kelvin probe measurement principles can be found in the above-referenced article by Weinzierl et al. in addition to "A Contactless Alternative to MOS Charge Measurements by Means of a Corona-Oxide-Semiconductor (COS) Technique," by R. L. Verkuil and M. S. Fung, *Electrochemical Society Extended Abstracts* No. 169, Vol. 88–1, 1998, pp. 261–262, "Replacing C-V Monitoring with Noncontact COS Charge Analysis," by K. D. Catmull, R. G. Cosway, B. A. Letherer, and G. S. Homer, *Solid State Technology*, June 1998, pp. 203–206, "(Review) Characterization and Production Metrology of Thin Transistor Gate Oxide Films," by Alain C. Diebold, David Venables, Yves Chabal, David Muller, Marcus Weldon, Eric Garfunkel, *Materials Science and Processing* 2, 1999, pp. 103–147, and U.S. Pat. No. 4,015,203 to Verkuil, U.S. Pat. No. 4,812,756 to Curtis et al., U.S. Pat. No. 5,485,091 to Verkuil, U.S. Pat. No. 5,767,691 to Verkuil, and U.S. Pat. No. 6,060,709 to Verkuil et al., all of which are incorporated by reference as if fully set forth herein.

One traditional method for measuring equivalent oxide thickness (EOT) involves depositing two different amounts of charge on the film and measuring the corresponding surface voltages. The EOT can be calculated from the ratio of the voltage difference to the charge difference. For non-leaky and relatively good quality films, the deposited charges have stable profiles and stay on the film for a relatively long time. Therefore, the measured amounts of charge and the surface voltages are substantially stable over time. But for leaky films such as very thin oxide films and thin oxynitride films, the charge on the film changes over time. As the time after the charge deposited on the film increases, the charge that is left on the film decreases due to leakage. Therefore, the measured surface voltage also decreases over time. Since the charge deposition gun and Kelvin probe measurement head are at different locations, regardless of how fast the gun or the measurement head moves, there will be measurement time delay. Thus, the measurement time delay and speeds at which the charge deposition gun and the Kelvin probe measurement head move have significant impacts on the measurement results.

Other methods are also proposed to try to correct the leakage effect. Examples of such methods are illustrated in U.S. patent application Ser. No. 10/616,086 entitled "Methods and Systems for Determining a Property of an Insulating Film," filed Jul. 9, 2003, which is incorporated by reference as if fully set forth herein. One of these methods is commercially available as the ACTIV™ EOT technology, which is incorporated in the Quantox XP system commercially available from KLA-Tencor. This method involves measuring surface voltage as a function of time to characterize the surface voltage decay due to leakage and using the surface voltage decay to correct the EOT. This method works for certain leaky films but for very leaky films, it may not give substantially accurate EOT values and may not have a good correlation to end-of-line C-V measurements.

SUMMARY OF THE INVENTION

An embodiment of the invention relates to a non-contact method for determining a parameter of an insulating film formed on a substrate. In one embodiment, the insulating film may be a leaky insulating film. In another embodiment, the insulating film may be a nitridated insulating film. The method includes measuring at least two surface voltages of the insulating film. The surface voltages are measured after different charge depositions on the insulating film. Measuring the surface voltages is performed in two or more sequences. A first of the two or more sequences may be a reverse of a second of the two or more sequences.

The different charge depositions include depositing a charge on the insulating film. The charge may be a positive charge, a negative charge, or some combination of a positive and a negative charge. In one embodiment, the different charge depositions may be substantially uniform across an area on which the different charge depositions are performed. In some embodiments, a time delay between the charge depositions and the surface voltage measurements is kept at a minimum such that the surface voltage measurements do not decrease substantially between the charge depositions and the measurements due to leakage in the insulating film. In another embodiment, the measurements may be performed in a minimum amount of time such that the surface voltage measurements do not decrease substantially during the measurements due to leakage in the insulating film.

The method also includes determining individual parameters for the two or more sequences from at least the two surface voltages and the different charge depositions. In addition, the method includes determining the parameter of the insulating film as an average of the individual parameters. In one embodiment, the average may be a weighted average. In some embodiments, the parameter may be equivalent oxide thickness (EOT). The parameter may be substantially independent of leakage in the insulating film. In another embodiment, the method may include measuring an optical thickness of the insulating film and determining a nitrogen dose, a nitrogen percentage, or a presence of nitrogen in the insulating film using the EOT and the optical thickness. In an additional embodiment, the method may include determining a nitrogen dose, a nitrogen percentage, or a presence of nitrogen in the insulating film using the EOT and a measure of leakage through the insulating film.

In some embodiments, the method may include altering a parameter of a process tool in response to the parameter of the insulating film using a feedback control technique or a feedforward control technique. The method may include any other steps of any methods described herein.

Another embodiment relates to a computer-implemented method that includes determining a characteristic of nitrogen in an insulating film using two parameters of the insulating film. In one embodiment, the insulating film may be a leaky insulating film. In some embodiments, the insulating film may be formed on a wafer using decoupled plasma nitridation. The two parameters may be selected from the group consisting of EOT, optical thickness, and a measure of leakage through the insulating film. The EOT may be substantially independent of the leakage in the insulating film. For example, the EOT may be measured as described herein. The characteristic may be a nitrogen dose, a nitrogen percentage, or a presence of nitrogen in the insulating film. In one embodiment, the method may include altering a parameter of a process tool in response to the characteristic of the insulating film using a feedback control technique or a feedforward control technique. This method may also include any other steps of any methods described herein.

An additional embodiment relates to a computer-implemented method that includes determining a characteristic of an insulating film using two parameters of the insulating film. The parameters of the insulating film may be selected from the group consisting of EOT, optical thickness, and a measure of leakage through the insulating film. The characteristic may be a dose of a component in the insulating film, a percentage of the component in the insulating film, or a presence of the component in the insulating film. In addition, this method may include any other steps of any methods described herein.

Yet another embodiment relates to a computer-implemented method that includes determining at least one composition parameter and physical thickness of an insulating film using a model and two or more parameters of the insulating film as input to the model. The two or more parameters are functions of at least the one composition parameter or the physical thickness. In one embodiment, the two or more parameters may include equivalent oxide thickness, optical thickness, a thickness measurement from tunneling electron microscopy, X-ray photoelectron spectroscopy, scanning capacitance microscopy, scanning force microscopy, energy dispersive X-ray spectroscopy, electron stimulated X-ray, X-ray diffraction, or X-ray reflectance, data from charge vs. voltage, current vs. voltage, or capacitance vs. voltage measurements, or information about a process used to form the insulating film. In some embodiments, at least the one composition parameter may be a nitrogen dose, a nitrogen percentage, or a presence of nitrogen in the insulating film. In another embodiment, at least the one composition parameter may be a characteristic of nitrogen or oxygen in the insulating film. In one such embodiment, the insulating film may be formed on a wafer using decoupled plasma nitridation or a high-k process. In another embodiment, the method may further include monitoring or controlling at least one parameter of a process tool using the at least one composition parameter or the physical thickness. For example, [N] percent information and/or film physical thickness information can be used in applications such as statistical process control (SPC) for process control in a semiconductor fab.

BRIEF DESCRIPTION OF THE DRAWINGS

Other objects and advantages of the invention will become apparent upon reading the following detailed description and upon reference to the accompanying drawings in which.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE INVENTION

The following description generally relates to the field of semiconductor wafer testing and, more particularly, to the measurement of the electrical thickness of both thin and thick, leaky and non-leaky insulating films and, for nitridation processes, a characteristic of nitrogen in the film. The methods described herein may be used to measure one or more parameters of an insulating film on the surface of a semiconducting wafer. In a common implementation, the methods described herein may be used as part of a process of semiconductor device manufacturing. For example, the insulating films may be used as part of a gate structure for a semiconductor device or integrated circuit.

Present technology for manufacturing integrated circuits and semiconductor devices makes extensive use of the formation of insulating films. These films may also be referred to as "dielectric layers." Such insulating films may be formed, for example, by deposition or thermal growth on a conductive or semiconductive substrate. In a typical implementation, a substrate may include, but is not limited to, silicon, epitaxial silicon, silicon-on-insulator ("SOI"), or another semiconductive or conductive material such as gallium arsenide or indium phosphide. The substrate may also include any substrate commonly found and/or processed in semiconductor fabrication facilities. Such substrates are commonly referred to as "wafers." Other conducting substrates are used as well, and the conducting substrates described herein may include any appropriate substrates known in the art.

In a typical implementation, an insulating film may include silicon dioxide ("$SiO_2$"), silicon nitride ("$Si_3N_4$"), or a nitrided form of amorphous $SiO_2$, which may be commonly referred to as oxynitride ("$SiO_xN_y$"). Many other materials are also commonly used. Such films frequently have relatively high insulating qualities. However, relatively thin films (i.e., films having a thickness of less than about 8 nm) may depart substantially from ideal insulating behavior. That is to say that such films may allow significant amounts of current to flow through the insulating film.

For insulating films that are not a form of $SiO_2$, significant departures from a perfect insulator may occur at a substantially greater thickness such as a thickness of greater than about 30 nm, or even greater than about 50 nm. Such less ideally insulating films may include materials commonly known as "high-k" or "low-k" insulators, where "k" refers to the real part of the dielectric constant as measured at electrical frequencies. A high-k dielectric material may include any material having a dielectric constant greater than about 3.9. Example of high-k materials include, but are not limited to, tantalum pentoxide ("$Ta_2O_5$"), hafnium dioxide ("$HfO_2$"), aluminum trioxide ("$Al_2O_3$"), and zirconium dioxide ("$ZrO_2$"). A low-k dielectric material may include any material having a dielectric constant less than about 3.9. Examples of low-k materials include, but are not limited to, proprietary materials known as Silc™, Black Diamond™, and Flare™. It is to be understood that the methodology described herein is not specific to any composition or thickness of the film(s) or sequence of films being measured. The embodiments described herein involve making measurements on the surface of an insulating film formed on a substrate which is to be taken to mean making the measurement on the uppermost layer of any film or stack of films that may be present at the measurement site.

It is a significant advantage to be able to directly measure electrical parameters of an insulating film since the end-usage of semiconductor products is electrical in nature. Making electrical measurements on the surface of a wafer typically involves a voltage measurement. In an ideal implementation, the voltage measurement is made in a non-contacting manner. There are obvious advantages to making such voltage measurements in a non-contacting manner.

Examples of technologies that provide measurement of voltages in a non-contacting manner include Kelvin probes, Monroe probes, and electrostatic force microscopy ("EFM"). Some of these technologies will be described in more detail herein. Other technologies are also known in the art.

Figure 1:
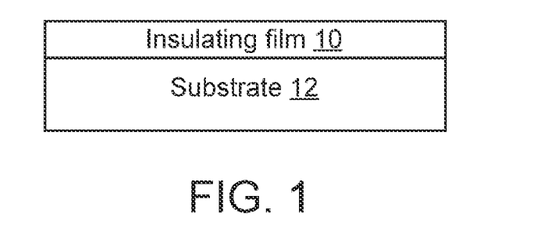
FIG. 1 is a schematic diagram illustrating a partial cross-sectional view of an embodiment of an insulating film formed on a substrate.
Figure 2:
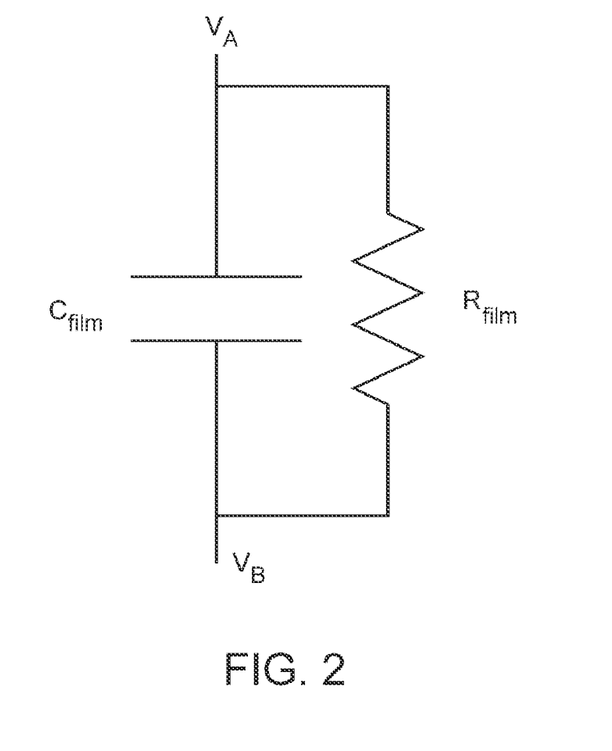
FIG. 2 is a schematic diagram of the insulating film formed on the substrate.

For the purposes of simplicity of illustration, FIG. 1 illustrates a single layer of insulating film 10 formed on substrate 12. The insulating film may be schematically illustrated as shown in FIG. 2, in which a resistance of the film, $R_{film}$, is electrically in parallel with a capacitance of the film, $C_{film}$. $R_{film}$ corresponds to the resistance of this film to current transport vertically through the film within a given test area, A. $R_{film}$ may vary with voltage as $R_{film}$=function ($V_{film}$). $C_{film}$ corresponds to the capacitance of the region of the insulating film under test. $R_{film}$ may be related to the film resistivity, $\rho_{film}$, by the following equation:

$$R_{film} = \rho_{film} * T_{film}/A, \quad (1)$$

where $T_{film}$ is the physical thickness of the film, and A is the cross-sectional area of the region of the insulating film being tested. As shown in FIG. 2, $V_A$ corresponds to the voltage potential at the top of the film, and $V_B$ corresponds to the voltage of the substrate underneath the film. $V_B$ will be considered to be at ground potential for the purpose of the immediate discussion.

In the absence of leakage, the voltage between points A and B, $V_{AB}$, may be defined by the equation for a parallel plate capacitor:

$$Q = V_{AB} * C_{film}, \quad (2)$$

where Q represents charge on the surface of the insulating film. By making depositions of charge, the total of which is recorded as $Q_i$ using a non-contacting technique and measuring subsequent voltage measurements of the potential, $V_{AB}$, recorded as $V_i$ using a non-contacting technique, the capacitance of the film, $C_{film}$, may be determined.

In many implementations, the initial charge of the surface is unknown, and equation 3 may be rewritten as:

$$Q_i = V_i * C_{film} + X_1, \quad (3)$$

where $X_1$ is an offset related to the initial charge on the surface of an insulating film and within the insulating film, but which is unimportant to this discussion. $C_{film}$ may be determined using a least-squares fit of any portion of $Q_i$–$V_i$ data with a slope being equal to $C_{film}$ according to equation 3. If the dielectric constant of the film is known or is assumed, an "electrical film thickness," $T_{film}$, may be determined from the capacitance. The capacitance of the film may be related to the electrical thickness using the equation:

$$T_{film} = \epsilon_0 * k * A / C_{film}, \quad (4)$$

wherein $\epsilon_0$ is the free space permittivity of vacuum, and k is the film relative dielectric constant described above. In a technologically feasible implementation, the voltages, $V_i$, corresponding to charge states, $Q_i$, may be measured at different times denoted as $t = t_i$.

Figure 3:
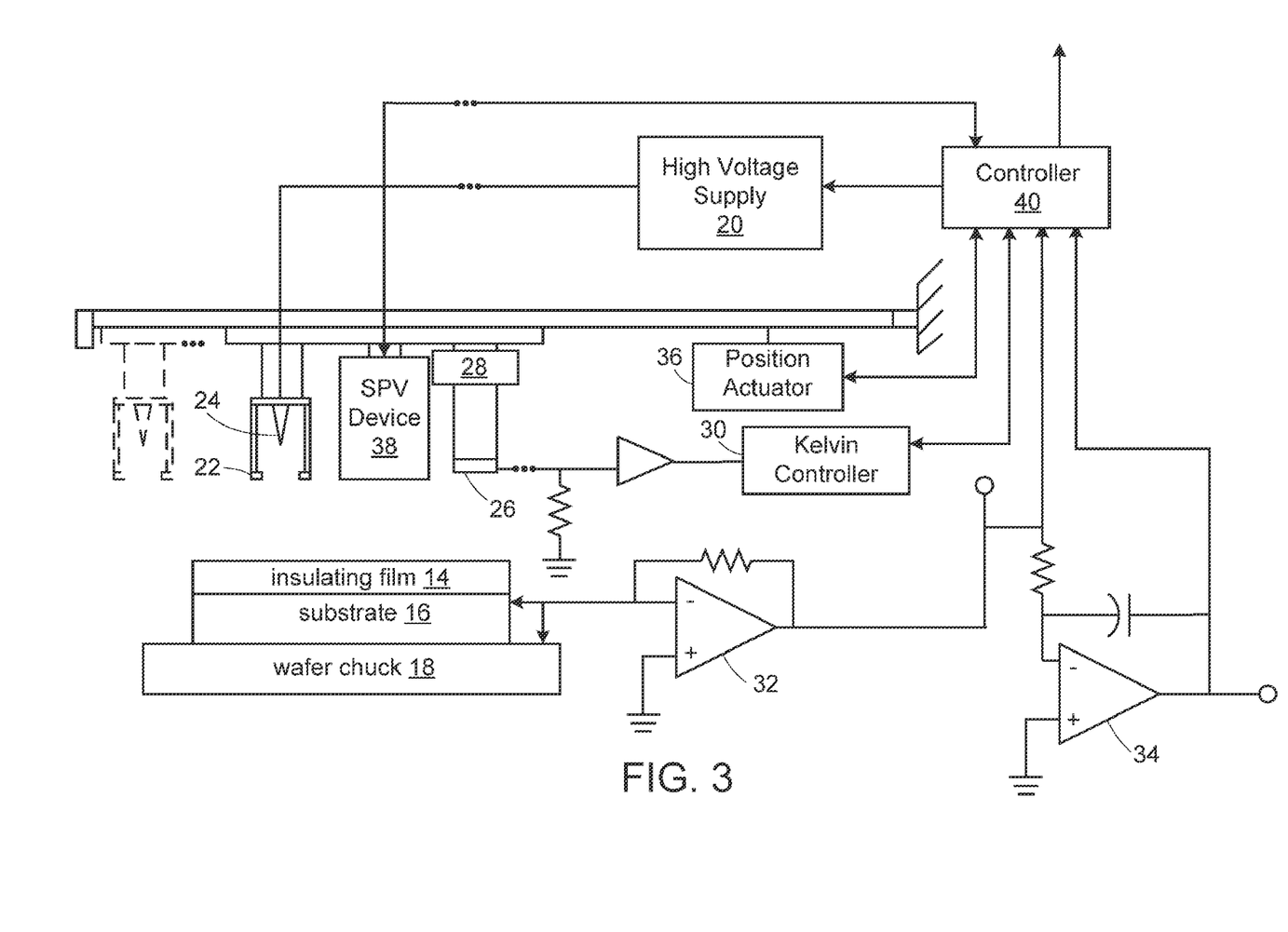
FIG. 3 is a schematic diagram of an embodiment of a system configured to measure charge density and voltage using non-contacting techniques.

An example of a system configured to measure charge density and voltage using non-contacting techniques is illustrated in FIG. 3. The system may be configured to measure current-voltage characteristics of insulating film 14 formed on substrate 16. The system may include wafer chuck 18 configured to hold substrate 16 during a measurement process. Wafer chuck 18 may also provide a grounding contact to substrate 16. The grounding contact may be obtained, for example, from a high pressure contact using a sharp tungsten carbide needle. The system may also include high voltage supply 20 coupled to corona gun 22. High voltage supply 20 may be configured to supply high voltage (i.e., about 6 kV to about 12 kV) to the corona gun to produce positive or negative corona charges depending on the polarity of supply 20. Corona gun 22 may include one or more needles 24 coupled to high voltage supply 20.

In addition, the system may include Kelvin probe 26. Kelvin probe 26 may include an electrode coupled to vibrator 28. Movement of probe 26 above a charged surface may result in an AC voltage representative of the potential of the charged surface. Kelvin controller 30 may be configured to convert an AC voltage to a signal corresponding to the voltage of the surface.

Current flowing through insulating film 14 and substrate 16 from corona gun 22 may be converted to a voltage by the current-to-voltage converter 32. This voltage (current) may be integrated by charge integrator 34 to provide a measure of the charge deposited by corona gun 22 on insulating film 14. The circuits, thus, are configured as a coulombmeter. The system may also include position actuator 36. Position actuator 36 may be configured to move corona gun 22 and Kelvin probe 26 over substrate 16, as shown in phantom in FIG. 3. The system may also include surface photo voltage (SPV) device 38. SPV device 38 may be configured to make an SPV measurement using a relatively high intensity light source such as a xenon flash tube.

The system may further include controller 40 configured to control operation of the system. Controller 40 may be configured to control position actuator 36 and high voltage supply 20 in response to Kelvin controller 30, the current-to-voltage converter 32, and the current-to-integrator 34. The controller may also be configured to provide a measurement of the current-voltage behavior of insulating film 14 and substrate 16. The controller may be, for example, a dedicated microprocessor-based controller or a general purpose computer.

Figure 4:
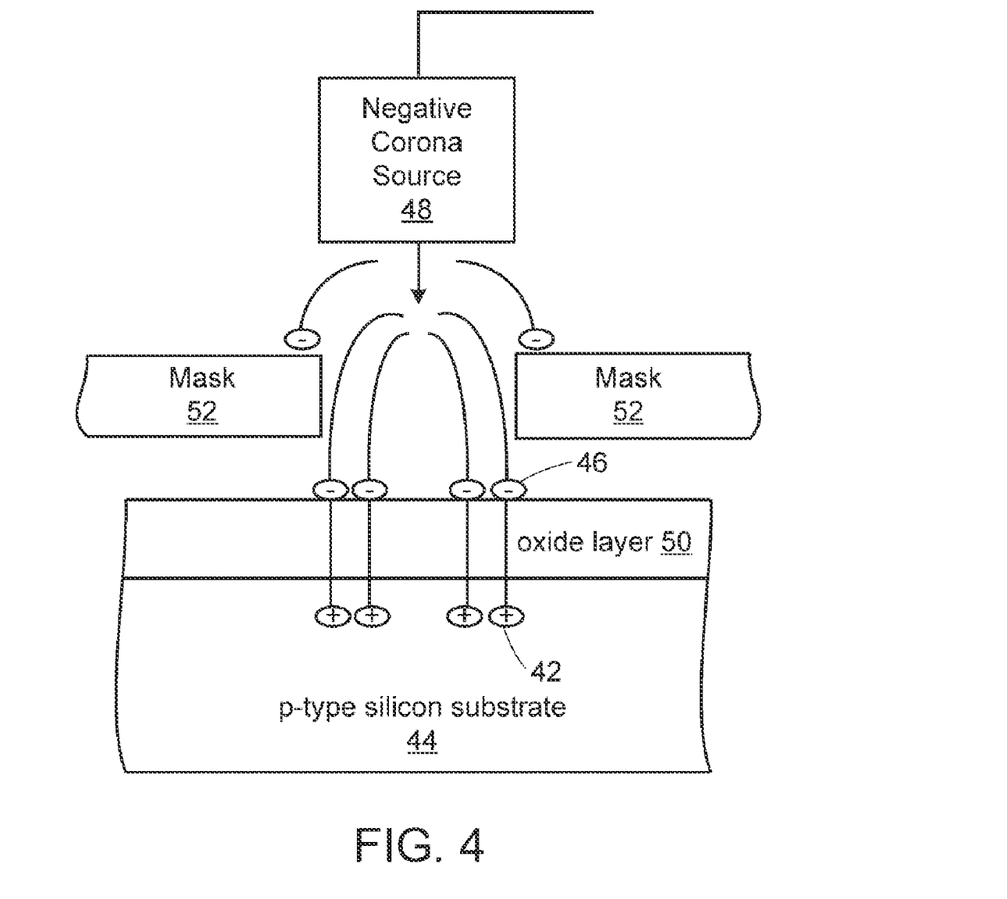
FIG. 4 is a schematic diagram illustrating an embodiment of a charge deposition on a surface of an insulating film using a corona source.

FIG. 4 illustrates an embodiment of a charge deposition on a surface of an insulating film using a corona source. As shown in FIG. 4, positive charge accumulation 42 in p-type silicon substrate 44 may result from the deposition of negative charges 46 from negative corona source 48 onto surface of oxide layer 50 overlying substrate 44. The corona discharge may be applied to the area of interest via mask 52. In one embodiment, it may be necessary for purposes of obtaining accurate thickness measurements, that a substantially uniform density of charge 46 be deposited through the aperture in mask 52.

Figure 5:
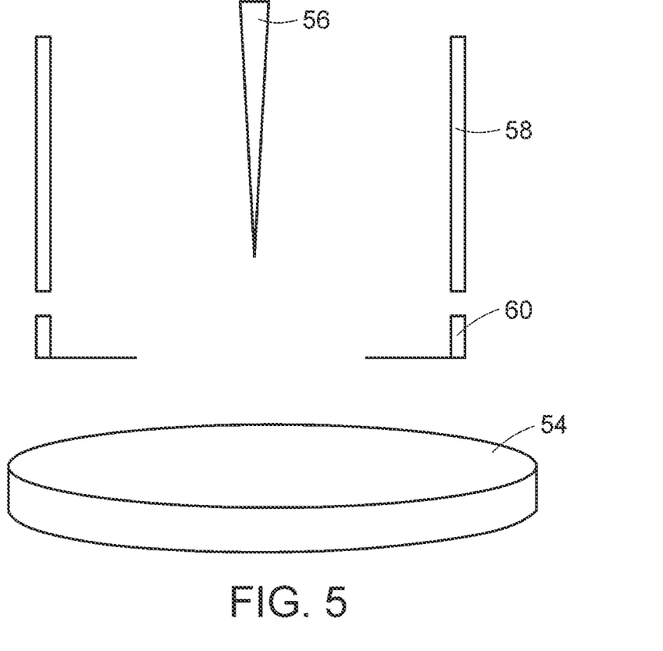
FIGS. 5 and 6 are schematic diagrams illustrating partial cross-sectional views of alternative embodiments of a corona source.
Figure 6:
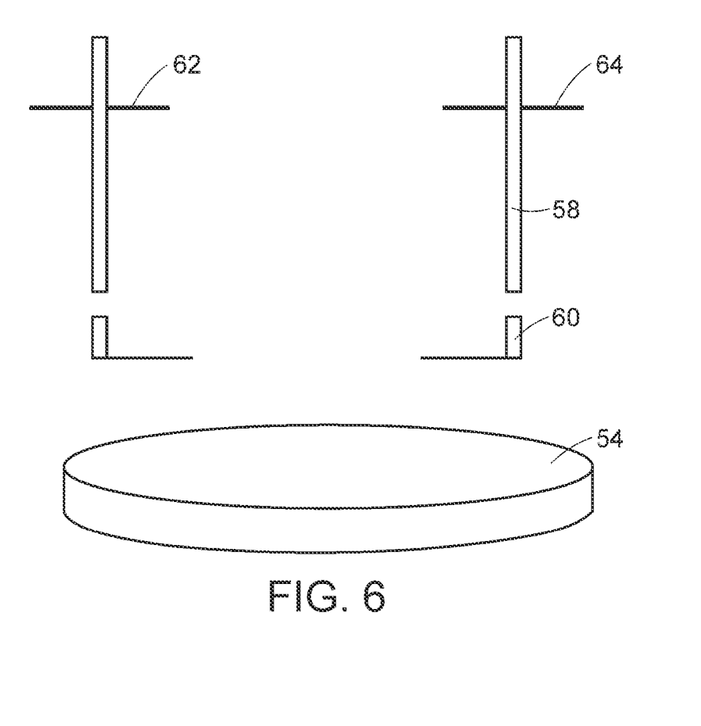

FIGS. 5 and 6 illustrate partial cross-sectional views of alternative embodiments of a corona source, which may be used to deposit a charge substantially uniformly over an area of specimen 54. Specimen 54 may include an insulating film and a substrate as described herein. The corona sources may be configured to provide a well-defined and substantial beam charge density (to minimize measurement time) having relative uniformity (for measurement accuracy) across the selected site of interest on specimen 54. As shown in FIG. 5, the corona source may include needle 56 and beam shaping electrodes 58 and 60. Beam shaping electrodes 58 and 60 may be arranged concentric with an axis of needle 56. Beam shaping electrodes 58 and 60 and the biasing voltages applied thereto may improve the corona charging capability of the gun in two important ways. First, lower electrode 60 may act as a mask for defining the diameter of the area of corona deposition. Second, the bias voltage on electrode 60 (same polarity as the corona ions) repels ions that normally would be captured by the edge of electrode 60 and directs them down to the specimen site with an enhanced density that abruptly ceases under the edge of electrode 60.

Upper electrode 58 may help to boost the efficiency of the corona source by being biased at a relatively high voltage (up to ±3 kV) with the same polarity as the corona ions. Potentials in the range of ±6–9 kV and up to ±1.5 kV are appropriate for needle 56 and mask electrode 60, respectively. This may result in an electric field configuration, in the upper region of the corona source, that prevents many of the ions from being captured by the upper electrode and directs them down to lower electrode 60 which, in turn, directs them to the specimen site. It should be noted that needle 56 and electrodes 58 and 60 may be supported and insulated from each other by suitable insulated support members (not shown) that may allow for the application of the necessary biases.

FIG. 6 is essentially the same as FIG. 5 except for the important difference that two facing and horizontal needles 62 and 64 are provided in FIG. 6 in lieu of the single vertical needle 56 of FIG. 5. The potential applied to needles 62 and 64 and electrodes 58 and 60 of FIG. 6 may be the same as the corresponding parts in the case of FIG. 5.

Additional examples of non-contact corona sources are illustrated in U.S. Pat. No. 4,599,558 to Castellano et al., U.S. Pat. No. 5,594,247 to Verkuil et al., and U.S. Pat. No. 5,644,223 to Verkuil and are incorporated by reference as if fully set forth herein. In an embodiment, a system as described herein, may include a non-contact work function sensor such as a Monroe probe in place of a Kelvin probe. Further examples of work function sensors that may be incorporated into the system are illustrated in U.S. Pat. No. 4,812,756 to Curtis et al., U.S. Pat. No. 5,650,731 to Fung, and U.S. Pat. No. 5,767,693 to Verkuil, which are incorporated by reference as if fully set forth herein. In addition, any other appropriate system and corona source known in the art may be used for carrying out a method as described herein. Furthermore, a system configured to perform the methods described herein may be coupled to a process tool. Examples of a process tool that the measurement system may be coupled to include, for example, a deposition tool, a thermal growth tool, an ion implantation tool, an anneal tool, and a decoupled plasma nitridation (DPN) tool.

Briefly, for a traditional Q-V measurement sequence, a charge is first deposited on an area of the film. A measurement head is then moved over the charged area, and the surface voltage is measured. From the measured surface voltages at two different deposited charges, $Q_1$ and $Q_2$, EOT can be measured. One such method is illustrated in U.S.

Patent Application Ser. No. 60/423,225 entitled "Methods for Non-Contacting Differential Voltage Measurements," filed Nov. 1, 2002, which is incorporated by reference as if fully set forth herein.

To overcome the leakage effect and to obtain substantially accurate EOT measurements on leaky insulating films, new methods that provide substantially accurate EOT measurements by leakage cancellation have been developed. The new methods are non-contact methods for determining a parameter of an insulating film formed on a substrate. In some embodiments, the insulating film may be a nitridated insulating film. In an embodiment, a method for determining a parameter such as EOT of an insulating film, which may be leaky or non-leaky, includes two or more measurement sequences. The measurement sequences include measuring at least two surface voltages, which are measured after different charge depositions on the insulating film. Although the methods described herein are described with respect to EOT, it is to be understood that the methods may also be used to determine other leakage-affected parameters of an insulating film.

One of the sequences may be similar to the above-mentioned sequence, but may involve two or more steps (e.g., deposit $Q_1$, measure $V_1$, deposit $Q_2$, measure $V_2$, . . . , deposit $Q_n$, measure $V_n$). Another of the sequences may be the reverse of the first measurement sequence but with different charges (e.g., deposit $Q_n'$, measure $V_n'$, . . . , deposit $Q_2'$, measure $V_2'$, deposit $Q_1'$, measure $V_1'$). The deposited charges, $Q_1$, $Q_2$, . . . , $Q_n$, etc. may be all positive, all negative, or some combination thereof. The deposited charge values can be in a certain pattern such as in a loop where $Q_n=Q_1$, or may monotonically increase or decrease, etc.

The method also includes determining individual parameters for the two or more sequences from the surface voltages and the different charge depositions. In addition, the method includes determining the parameter of the insulating film as an average of the individual parameters. Therefore, EOT may be determined from the different sequences, which may or may not be determined as a weighted average of the individual EOT measurements.

Figure 7:
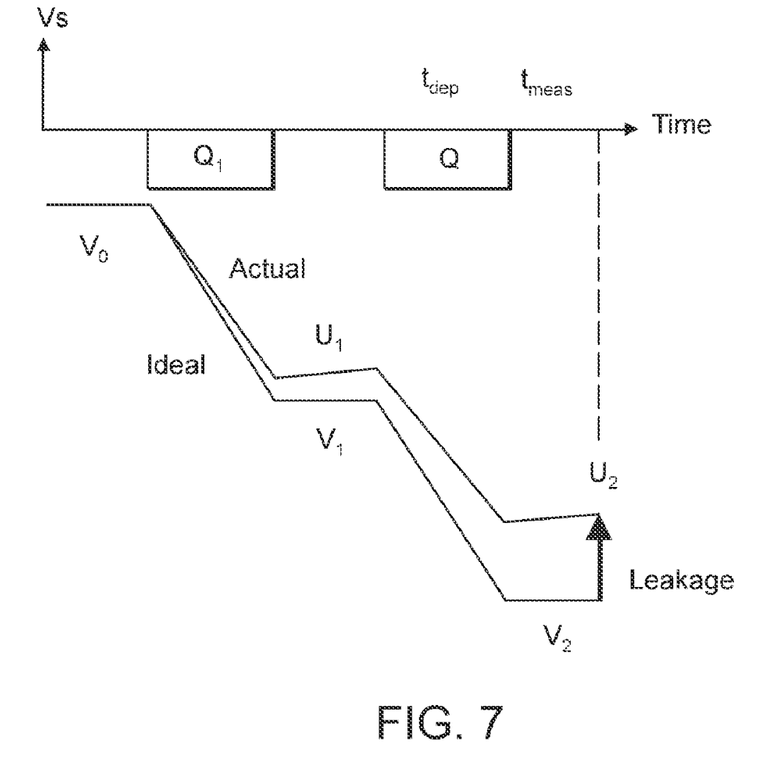
FIG. 7 is an illustration of the effects of charge leakage in an insulating film on surface voltage measurements.

This approach, to the first order, essentially cancels the leakage effect. FIG. 7 is an illustration of the charge leakage effect on surface voltage measurements. For non-leaky films, the charges stay on the film, and the surface voltage is stable over time (i.e., $V_0$, $V_1$, and $V_2$ are stable). But for leaky films, the surface voltage values ($U_1$, $U_2$) change over time, as shown in FIG. 7. Therefore, simply measuring $U_1$ and $U_2$ (corresponding to $Q_1$ and $Q_2$, respectively) will not produce an accurate EOT measurement. For example, the surface voltages and, therefore, EOT results from this measurement will always be smaller than their real values due to leakage. The new measurement method, however, adds other sequences to effectively cancel out the leakage effect. As such, the EOT is substantially independent of leakage in the insulating film. Therefore, the average or the weighted average of EOTs from different sequences will provide the real EOT value of the insulating film.

The corona gun used to deposit the charges preferably has a relatively high deposition rate. The corona gun profile is preferably substantially uniform across an area on which the charge depositions are performed since multiple back-and-forth depositions are performed. In addition, the Kelvin probe measurement head preferably has a relatively fast response time and a relatively high sampling rate to reduce the delay time thereby reducing the leakage effect on the surface voltage measurements.

The method includes calibrating the system's deposition gun and the measurement head. For the corona gun, the goal is to adjust the corona gun deposition rate to a known value with a relatively good charge profile. For the measurement head, the goal is to adjust the Kelvin probe sensitivity close to a known value. Without calibration, the accuracy of the deposited charges and the surface voltage measurements will be unknown.

The corona gun calibration may be performed in many different ways. One calibration method is to use a non-leaky, substantially pure oxide film with known thickness. The oxide film may be formed on a wafer. The thickness of the oxide film and the deposited charge amount or surface voltage selected for the first measurement to be performed may be used as the calibration criteria. The corona gun deposition rate may be calibrated with an internal detector (as in the case of the Quantox™ system). The known thickness of the oxide film may be used to measure EOT with a measurement sequence (e.g., a 2-sequence measurement with $Q_1=Q_1'$, $Q_2=Q_2'$, and $Q_3=Q_3'=Q_1$). The deposition rate may be fine-tuned to make $V_1=V_1'$, $V_2=V_2'$, and $V_3=V_3'=V_1$. The Kelvin probe measurement head may be calibrated using an internal calibration mechanism such as the internal calibration mechanism incorporated in the Quantox™ system.

Once the system is calibrated, the EOT measurement may be performed using the following steps. The following example is a 2-sequence measurement with $V_1=V_1'$, $V_2=V_2'$, and $V_3=V_3'=V_1$. However, it is to be understood that the EOT measurement may include more than 2 sequences. For example, the number of measurement sequences and the number of steps in each measurement sequence may vary depending upon the application. In one example, if a non-leaky film is being measured, then one or two sequences and two steps may be used to determine the EOT. Alternatively, if a leaky film is being measured, then two or more sequences and two or more steps may be used to determine the EOT.

In some embodiments, the method includes pre-biasing the measurement site prior to measurements. The measurement site may be pre-biased to a predetermined value of a particular parameter as the starting reference point. The parameter may be surface photo-voltage (SPV), surface voltage ($V_s$), deposited charge (Q), or other combinations of different parameters. If the film is substantially leaky, the predetermined value for pre-biasing may be the initial SPV level. Pre-biasing generally involves moving the corona gun and measurement head back and forth several times for depositing and measuring until the parameter reaches the predetermined value. Another option is to pre-bias the measurement site in a repeated format, which may be commonly referred to as pre-conditioning. Pre-conditioning may be performed with larger amounts of positive and negative charges in series with a few repeats on the same measurement site. After pre-conditioning, the measurement site may be pre-biased to the predetermined value for the parameter.

The method also includes depositing charge $Q_1$ on the measurement site. For example, the corona gun may be moved above the previously pre-biased site. A charge $Q_1$ may then be deposited on the measurement site. In one embodiment, the charge $Q_1$ may be implemented by a blanket charge since the EOT may be less sensitive to the initial $Q_1$. Depositing a blanket charge will increase the throughput of the measurement process. The charge $Q_1$ may be measured either with a coulombmeter (a "Q-meter") or determined using the deposition rate and the deposition time. In addition, the method includes measuring a surface voltage $V_1$ of the measurement site. For example, the measurement head may be moved above the measurement site to measure the surface voltage. The time delay between depositing the charge on the measurement site and measuring the surface voltage is preferably as short as possible to reduce the effects of leakage on the measurements. In this manner, the surface voltages may not decrease substantially between the charge depositions and the surface voltage measurements due to leakage in the insulating film. In addition, measuring the surface voltages may be performed in a minimum amount of time such that the surface voltages do not decrease substantially during the surface voltage measurements due to leakage in the insulating film.

The method further includes depositing charge $Q_2$ on the measurement site. In this step, the corona gun may be moved back above the measurement site. A charge amount of approximately $Q_2-Q_1$ may be deposited on the measurement site such that the total charge deposited on the site is about $Q_2$. The measurement head may then be moved above the measurement site, and $V_2$ of the measurement site may be measured.

The method also includes depositing charge $Q_3$ on the measurement site, where $Q_3=Q_1$. In this step, the corona gun may be moved back above the measurement site. A charge amounting to approximately $Q_1-Q_2$ may be deposited on the measurement site such that the total charge deposited on the measurement site is $Q_3=Q_1$. The surface voltage $V_3$ of the measurement site may then be measured as described above. Therefore, the second and third measurements form a sequence that is the reverse of the first and second measurement sequence. In this manner, the leakage effects can be essentially cancelled out thereby allowing more accurate measurements of EOT.

After a sufficient number of surface voltage measurements have been performed, the measurement site may be post-biased to the initial reference (pre-bias) point. Post-measurement biasing may be performed as described above to bias the measurement site to its original state or to a known state.

The EOT for the insulating film may be determined using the following equations:

$$EOT_1 = C * \frac{V_2 - V_1}{Q_2 - Q_1}, \qquad (5)$$

$$EOT_2 = C * \frac{V_3 - V_2}{Q_3 - Q_2} = C * \frac{V_1 - V_2}{Q_1 - Q_2}, \text{ and} \qquad (6)$$

$$EOT = \frac{(EOT_1 + EOT_2)}{2}. \qquad (7)$$

In this case, the EOT may be determined as a simple non-weighted average of the two individual EOTs that are determined for each sequence of measurements. Alternatively, the EOT may be determined as a weighted average using the following equation:

$$EOT = \frac{(EOT_1 + \zeta * EOT_2)}{1 + \zeta} \qquad (8)$$

where $\zeta$ is a weight factor. Whether a non-weighted average or a weighted average is used to determine the EOT may vary depending upon the application.

The following method may be used for a 4-sequence measurement. The method includes pre-biasing a measurement site on an insulating film to a known state as a starting reference point. Pre-biasing may be performed as described above. The method also includes depositing charge $Q_1$ on the measurement site and measuring surface voltage $V_1$. In addition, the method includes depositing charge $Q_2$ on the measurement site and measuring surface voltage $V_2$. The method further includes depositing charge $Q_3$ on the measurement site and measuring surface voltage $V_3$. Depositing the charges may be performed as described above. In addition, measuring these surface voltages may be performed as described above.

The method may then include pre-biasing the measurement site to the starting reference point. In addition, charge $Q_4$ may be deposited on the measurement site after pre-biasing, and surface voltage $V_4$ may be measured. Charge $Q_5$ may then be deposited on the measurement site, and surface voltage $V_5$ may be measured. The method may also include depositing charge $Q_6$ on the measurement site, and measuring surface voltage $V_6$. In addition, the method may include post-biasing the measurement site to the starting reference point or a known value.

The EOT of the insulating film may be measured using the following equations:

$$EOT_1 = C * \frac{V_2 - V_1}{Q_2 - Q_1}, \qquad (9)$$

$$EOT_2 = C * \frac{V_3 - V_2}{Q_3 - Q_2}, \qquad (10)$$

$$EOT_3 = C * \frac{V_5 - V_4}{Q_5 - Q_4}, \qquad (11)$$

$$EOT_4 = C * \frac{V_6 - V_5}{Q_6 - Q_5}, \text{ and} \qquad (12)$$

$$EOT = \frac{(EOT_1 + EOT_2 + EOT_3 + EOT_4)}{4}. \qquad (13)$$

In this case, EOT is a simple non-weighted average of the four individual EOT measurements. Alternatively, the EOT may be determined as a weighted average as described above.

Figure 8:
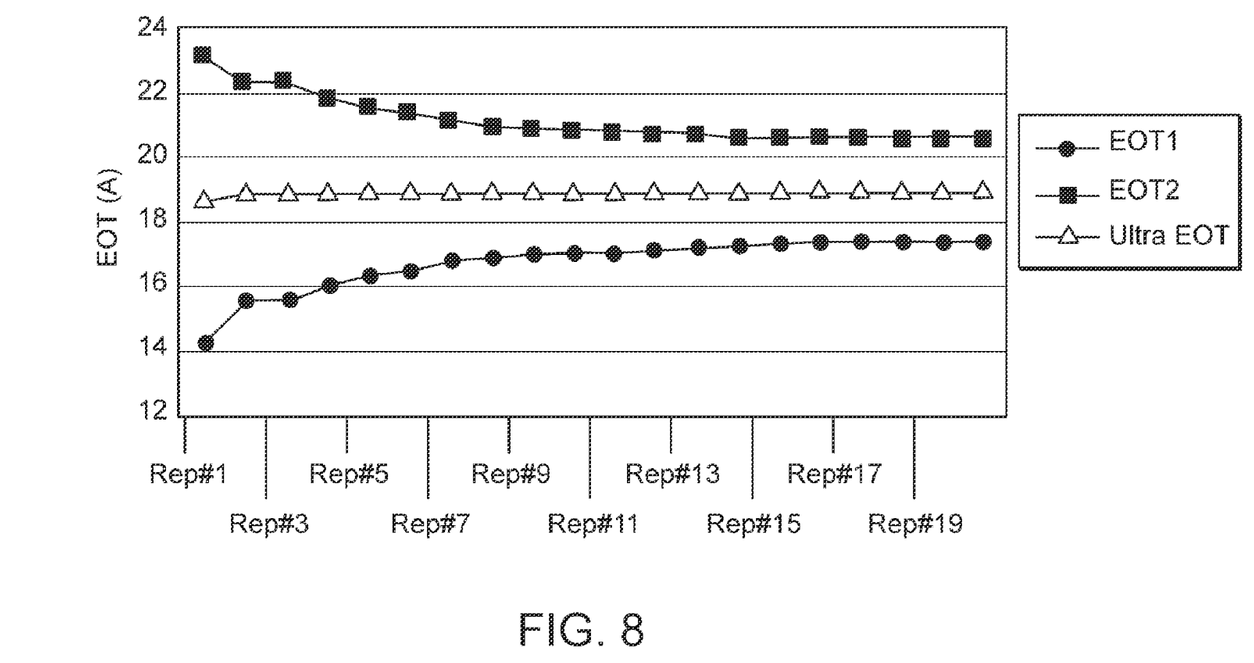
FIG. 8 is a graph illustrating the differences between EOT values measured using the embodiments described herein and EOT values measured using other methods known in the art.

FIG. 8 shows typical EOT results determined using the methods described herein, which were performed on the same site of an insulating film using repeat measurements. "EOT$_1$" and "EOT$_2$" represent EOT results measured using only one sequence of measurements, which included only two measurement steps. The measurement sequence for EOT$_1$ is the reverse of the measurement sequence for EOT$_2$. "Ultra EOT" represents measurement results using the methods described herein. As shown in FIG. 8, EOT$_1$ and EOT$_2$ show large changes in the repeat measurements on the same site. However, the EOT measured using the methods described herein is substantially stable and consistent across the same site repeat measurements.

Recently, decoupled plasma nitridation (DPN) is becoming increasingly used in gate processes to produce relatively thin nitridated insulating films. Examples of DPN tools that are commercially available include the DPN Centura 200 and the DPN Centura 300 systems available from Applied Materials, Santa Clara, Calif. Therefore, there is an increasing need to be able to perform EOT measurements of these nitridated films. However, since this type of insulating film is substantially leaky and is prone to defects more so than other insulating films, traditional EOT measurements cannot provide accurate EOT values of nitridated insulating films. However, the methods described herein may be used to substantially accurately determine the EOT of nitridated insulating films.

In addition, a characteristic of nitrogen in the nitridated films is another parameter that is useful to know for process control purposes. Generally, there are only a few analytical tools that are commercially available and that can be used to measure chemical composition such as electron stimulated x-ray (ESX) systems, x-ray photoelectron spectroscopy (XPS), and electron probe micro-analyzers (EPMA), which are commercially available from CAMECA, France. However, there is also a need for a method for determining a nitrogen dose, a nitrogen percentage, and/or a presence of nitrogen in an insulating film either directly or indirectly from the measurement since nitrogen content of the insulating film is an important parameter for nitridation process control.

Nitrogen percentage in a nitridated insulating film may be determined using the EOT of the insulating film, which is determined as described herein, and an optical thickness of the insulating film. The optical thickness may be determined using any optical technique known in the art such as reflectometry and ellipsometry. One example of a commercially available system that may be used to measure an optical thickness of an insulating film is the ASET F5x tool, which is commercially available from KLA-Tencor. The following equations define a model based on the linear relationship between nitrogen ([N]) and k, and [N] and n. These parameters have the following relationships:

$$k_{SiON} = (1-x)*k_{oxide} + x*k_{nitride}, \quad (14)$$

$$n_{SiON} = (1-x)*n_{oxide} + x*n_{nitride}, \quad (15)$$

$$EOT = \frac{k_{SiON}}{k_{oxide}} * T_{phy}, \quad (16)$$

$$T_{opt} = \frac{n_{SiON}}{n_{oxide}} * T_{phy}, \text{ and} \quad (17)$$

$$[N]\% = \frac{400*x}{9 - 2*x}. \quad (18)$$

where $k_{SiON}$ is the extinction coefficient of SiON, $k_{oxide}$ is the extinction coefficient of oxide, $k_{nitride}$ is the extinction coefficient of nitride, $n_{SiON}$ is the index of refraction of SiON, $n_{oxide}$ is the index of refraction of oxide, $n_{nitride}$ is the index of refraction of nitride, $T_{phy}$ is the physical thickness of the nitrided insulating film, and $T_{opt}$ is the optical thickness of the insulating film. Therefore, the above method may also be used to simply determine if nitrogen is present in the insulating film. In a similar manner, nitrogen dose in a nitridated insulating film as well as the film physical thickness may also be determined.

Although the method and equations are described above with respect to SiON, it is to be understood that the methods described herein may be equally applied to any other nitridated insulating films known in the art. In addition, although the method and equations are described herein with respect to nitrogen, it is to be understood that the methods described herein may be equally used to determine another characteristic of a composition of an insulating film (e.g., dose of a component, percentage of a component, or presence of a component in the insulating film). As used herein, the term "component" is used to refer to any elemental component, ionic component, or molecular component that forms a portion of an insulating film.

From the ratio of EOT/T$_{opt}$, we can solve the above equations for [N]%. The results obtained by this method have been shown to correlate very well to XPS measurement results. In a similar manner, a nitrogen dose in the insulating film, a concentration of nitrogen in the insulating film, and/or a presence of nitrogen in the insulating film may be determined. Another method for determining the [N]% is to use tunneling theory in combination with the Quantox™ ACTIV J$_g$ Index and the new EOT measurement or optical thickness, which may be measured as described above. More information on tunneling theory may be found in "Semiconductor Material and Device Characterization" by Dieter K. Schroder; 2$^{nd}$ edition (June 1998). The ACTIV J$_g$ Index provide a description or a measure of leakage through an insulating film. For example, when the J$_g$ Index is high, there is less leakage through an insulating film, and when the J$_g$ Index is low, there is more leakage through an insulating film. Examples of methods for describing leakage through an insulating film are described in U.S. Pat. No. 6,097,196 to Verkuil et al. and U.S. Patent Application Ser. No. 60/423,225 entitled "Methods for Non-Contacting Differential Voltage Measurements," filed Nov. 1, 2002, which are incorporated by reference as if fully set forth herein. One advantage of using ACTIV J$_g$ Index and EOT is that the [N]% information can be obtained with only one electrical measurement tool instead of combination of both electrical and optical measurement tools.

The methods described herein are particularly useful for leaky films such as insulating films produced by a DPN process. However, the methods described herein may be used for measurements of non-leaky films as well. In addition, the results have been show to correlate very well to end-of-line capacitance vs. voltage (C-V) measurement results.

The methods described herein are not necessarily limited to the EOT and optical thickness or leakage measurements. It is to be understood that the method also applies to a general case where two or more parameters can be used as input to a model to determine film physical thickness and at least one composition parameter such as a characteristic of nitrogen or oxygen in films formed by DPN and high-k processes. The parameters used in the model are functions of physical thickness and other composition parameters. For example, the parameters other than EOT and optical thickness that are functions of, but not limited to, film physical thickness may be obtained from tunneling electron microscopy (TEM), XPS, scanning capacitance microscopy (SCM), scanning force microscopy (SFM), energy dispersive X-ray spectroscopy (EDS), ESX, X-ray diffraction (XRD), X-ray reflectance (XRR), etc., data from Q-V, I-V, C-V curves and the information about the process used to form the film (e.g., one or more process conditions such as pressure, time, power, etc). The model may include equations such as those described above. The output from the model includes film physical thickness and other composition (e.g., nitrogen percentage and dosage information).

In an embodiment, the method may include altering a parameter of a process tool in response to one or more parameters of an insulating film such as capacitance, dielectric constant, equivalent oxide thickness of the insulating film or a characteristic of nitrogen in the insulating film (e.g., nitrogen dose, nitrogen percentage, or a presence of nitrogen in the insulating film) using a feedback control technique or a feedforward control technique. In another embodiment, the method may further include monitoring or controlling at least one parameter of a process tool using the at least one composition parameter, the physical thickness, and/or any another characteristic of the insulating film described herein. For example, [N] percent information and/or film physical thickness information can be used in applications such as statistical process control (SPC) for process control in a semiconductor fab.

The process tool may be, for example, a chemical vapor deposition (CVD) tool, a physical vapor deposition (PVD) tool, an atomic layer deposition (ALD) tool, a thermal growth tool, an ion implantation tool, an anneal tool, or a DPN tool. In this manner, a parameter of a process tool may be altered for forming the insulating film on additional substrates. The process tool may also include a process tool used for further processing of the substrate on which the measured insulating film is formed. For example, such a process tool may be a chemical-mechanical polishing (CMP) tool or an anneal tool such as a rapid thermal processing (RTP) tool. In this manner, a parameter of a process tool may be altered for further processing of the substrate on which the measured insulating film is formed. In a further embodiment, a processor as described herein may be coupled to the process tool and may be configured to alter a parameter of the process tool in response to at least one of the parameters of the insulating material using a feedback control technique or a feedforward control technique.

Program instructions implementing methods such as those described above may be transmitted over or stored on a carrier medium. The carrier medium may be a transmission medium such as a wire, cable, or wireless transmission link, or a signal traveling along such a wire, cable, or link. The carrier medium may also be a storage medium such as a read-only memory, a random access memory, a magnetic or optical disk, or a magnetic tape.

In an embodiment, a computer system may be configured to execute the program instructions to perform a computer-implemented method according to the above embodiments. The computer system may take various forms, including a personal computer system, mainframe computer system, workstation, network appliance, Internet appliance, personal digital assistant ("PDA"), television system or other device. In general, the term "computer system" may be broadly defined to encompass any device having a processor, which executes instructions from a memory medium.

The program instructions may be implemented in any of various ways, including procedure-based techniques, component-based techniques, and/or object-oriented techniques, among others. For example, the program instructions may be implemented using ActiveX controls, C++ objects, JavaBeans, Microsoft Foundation Classes ("MFC"), or other technologies or methodologies, as desired.

Further modifications and alternative embodiments of various aspects of the invention may be apparent to those skilled in the art in view of this description. For example, non-contact methods for measuring electrical thickness and determining nitrogen content of insulating films are provided. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A non-contact method for determining a parameter of an insulating film formed on a substrate, comprising:
   measuring at least two surface voltages of the insulating film, wherein the surface voltages are measured after different charge depositions on the insulating film, and wherein said measuring is performed in two or more sequences;
   determining individual parameters for the two or more sequences from the at least two surface voltages and the different charge depositions; and
   determining the parameter of the insulating film as an average of the individual parameters.

2. The method of claim 1, wherein the average is a weighted average.

3. The method of claim 1, wherein the insulating film is a leaky insulating film.

4. The method of claim 1, wherein the insulating film is a nitridated insulating film.

5. The method of claim 1, wherein a first of the two or more sequences is a reverse of a second of the two or more sequences.

6. The method of claim 1, wherein the parameter is equivalent oxide thickness.

7. The method of claim 1, wherein the parameter is substantially independent of leakage in the insulating film.

8. The method of claim 1, wherein a time delay between the different charge depositions and said measuring is kept at a minimum such that the at least two surface voltages do not decrease substantially between the different charge depositions and said measuring due to leakage in the insulating film.

9. The method of claim 1, wherein said measuring is performed in a minimum amount of time such that the at least two surface voltages do not decrease substantially during said measuring due to leakage in the insulating film.

10. The method of claim 1, wherein the different charge depositions comprise depositing a charge on the insulating film, and wherein the charge comprises a positive charge, a negative charge, or some combination of a positive and a negative charge.

11. The method of claim 1, wherein the different charge depositions are substantially uniform across an area on which the different charge depositions are performed.

12. The method of claim 1, wherein the parameter is equivalent oxide thickness, the method further comprising measuring an optical thickness of the insulating film and determining a nitrogen dose, a nitrogen percentage, or a presence of nitrogen in the insulating film using the equivalent oxide thickness and the optical thickness.

13. The method of claim 1, wherein the parameter is equivalent oxide thickness, the method further comprising determining a nitrogen dose, a nitrogen percentage, or a presence of nitrogen in the insulating film using the equivalent oxide thickness and a measure of leakage through the insulating film.

14. The method of claim 1, further comprising altering a parameter of a process tool in response to the parameter of the insulating film using a feedback control technique or a feedforward control technique.

15. A computer-implemented method, comprising determining a characteristic of nitrogen in an insulating film using two parameters of the insulating film selected from the group consisting of equivalent oxide thickness, optical thickness, and a measure of leakage through the insulating film, wherein the characteristic comprises a nitrogen dose, a nitrogen percentage, or a presence of nitrogen in the insulating film.

16. The method of claim 15, wherein the equivalent oxide thickness is substantially independent of the leakage in the insulating film.

17. The method of claim 15, wherein the insulating film is a leaky insulating film.

18. The method of claim 15, wherein the insulating film is formed on a wafer using decoupled plasma nitridation.

19. The method of claim 15, further comprising altering a parameter of a process tool in response to the characteristic using a feedback control technique or a feedforward control technique.

20. A computer-implemented method, comprising determining a characteristic of an insulating film using two parameters of the insulating film selected from the group consisting of equivalent oxide thickness, optical thickness, and a measure of leakage through the insulating film, wherein the characteristic comprises a dose of a component in the insulating film, a percentage of the component in the insulating film, or a presence of the component in the insulating film.

21. A computer-implemented method, comprising determining at least one composition parameter and physical thickness of an insulating film using a model and two or more parameters of the insulating film as input to the model, wherein the two or more parameters are functions of the at least one composition parameter or the physical thickness, and wherein at least one of the two or more parameters is from a non-contact electrical measurement.

22. The method of claim 21, wherein the at least one composition parameter comprises a nitrogen dose, a nitrogen percentage, or a presence of nitrogen in the insulating film.

23. The method of claim 21, wherein the two or more parameters comprise equivalent oxide thickness, optical thickness, a thickness measurement from tunneling electron microscopy, X-ray photoelectron spectroscopy, scanning capacitance microscopy, scanning force microscopy, energy dispersive X-ray spectroscopy, electron stimulated X-ray, X-ray diffraction, or X-ray reflectance, data from charge vs. voltage, current vs. voltage, or capacitance vs. voltage measurements, or information about a process used to form the insulating film.

24. The method of claim 21, wherein the at least one composition parameter comprises a characteristic of nitrogen or oxygen in the insulating film, and wherein the insulating film is formed on a wafer using decoupled plasma nitridation or a high-k process.

25. The method of claim 21, further comprising monitoring or controlling at least one parameter of a process tool using the at least one composition parameter or the physical thickness.

* * * * *